United States Patent [19]

Moehring

[11] Patent Number: 4,846,162

[45] Date of Patent: Jul. 11, 1989

[54] ORTHOPEDIC NAIL AND METHOD OF BONE FRACTURE FIXATION

[76] Inventor: H. David Moehring, 4215 Crestline, Ann Arbor, Mich. 48103

[21] Appl. No.: 95,887

[22] Filed: Sep. 14, 1987

[51] Int. Cl.$^4$ ............................................. A61B 17/58
[52] U.S. Cl. ........................... 128/92 YZ; 128/92 YY; 128/92 VD
[58] Field of Search ........... 128/92 Y, 92 YZ, 92 YY, 128/92 YK, 92 VD

[56] References Cited

U.S. PATENT DOCUMENTS

| | | | |
|---|---|---|---|
| 2,518,019 | 8/1950 | Kane | 128/92 YZ |
| 2,695,607 | 11/1954 | Hipps et al. | 128/20 |
| 2,812,761 | 11/1957 | Palkovitz | 128/92 Z |
| 2,985,168 | 5/1961 | Jonas et al. | 128/83 |
| 3,256,877 | 6/1966 | Haboush | 128/92 |
| 3,334,624 | 8/1967 | Schneider et al. | 128/92 YZ |
| 4,237,875 | 12/1980 | Termanini | 128/92 BA |
| 4,275,717 | 6/1981 | Bolesky | 128/92 YK X |
| 4,281,649 | 8/1981 | Derweduwen | 128/92 |
| 4,475,545 | 10/1984 | Ender | 128/92 YY |
| 4,522,201 | 6/1985 | Tongue | 128/92 YK X |
| 4,574,795 | 3/1986 | Georges | 128/92 |
| 4,622,959 | 11/1986 | Marcus | 128/92 VD X |
| 4,697,585 | 10/1987 | Williams | 128/92 YY X |

FOREIGN PATENT DOCUMENTS

| | | | |
|---|---|---|---|
| 118778 | 2/1984 | European Pat. Off. | 128/92 YY |
| 2359644 | 7/1975 | Fed. Rep. of Germany | 128/92 YY |
| 874049 | 10/1981 | U.S.S.R. | |
| 992042 | 2/1983 | U.S.S.R. | |
| 868185 | 12/1959 | United Kingdom . | |
| 2069846 | 9/1981 | United Kingdom | 128/92 VD |

OTHER PUBLICATIONS

Russell-Taylor Interlocking Nail System Instruction Booklet (Publication date unknown).

Primary Examiner—Robert A. Hafer
Assistant Examiner—Kevin G. Rooney
Attorney, Agent, or Firm—Price, Heneveld, Cooper, DeWitt & Litton

[57] ABSTRACT

An orthopedic nail for intramedullary fixation of fractures in long bones has an axially outwardly opening mouth in a first end thereof including a pair of side edge portions and an inward bight portion. A method of fixation of a fracture of a long bone includes driving a distal fastener transverse the bone on a medial frontal plane and axially inserting the mouth end of the nail into the medullary canal with the mouth on the same plane as the distal fastener. The fastener should be received within the mouth and seated against the bight portion due to the axial movement of the nail. A special jig is provided for accurately locating a second distal fastener if one is indicated. A retractable insertion device covers the mouth during nail insertion to reduce the likelihood of snagging vessels.

29 Claims, 3 Drawing Sheets

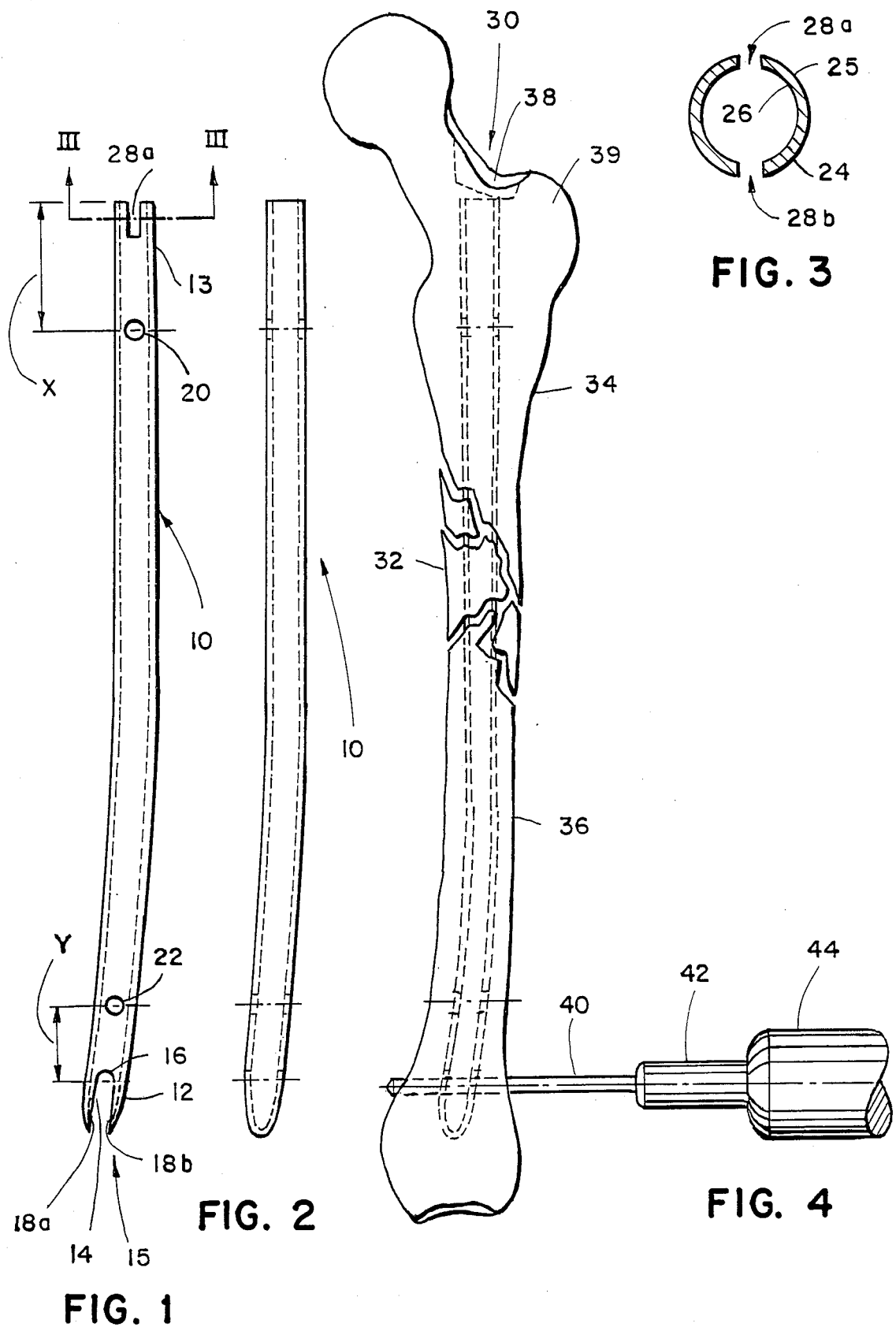

ORTHOPEDIC NAIL AND METHOD OF BONE FRACTURE FIXATION

BACKGROUND OF THE INVENTION

This invention relates to an intramedullary method and apparatus for fixation of a fracture in a long bone and in particular to a method and apparatus of the type that reduces the fracture and prevents shortening of the bone segments through the use of a locked intramedullary nail.

A severely comminuted fracture in a long bone such as a tibia or femur, has a tendency to cause the bone segments created by the fracture to compress, shortening the length of the bone. Traditional treatment to prevent such compression is by skeletal traction. A known alternative is to use a cannulated intramedullary nail that is inserted into an opening made in one end of the bone and looked to the bone segments. A guide wire is first inserted in the opening, that is typically made in the proximal end of the bone, and into the distal bone fragment significantly past the fracture site. The guide wire guides the cannulated nail past the fracture site. Although the intramedullary nail substantially occupies the medullary canal, it is only capable of retaining length and preventing excessive shortening if the bone segments are appropriately fastened, or locked, to the nail.

The problem in such a locked intramedullary nail technique is locating the distal aperture(s) in the nail and successfully aligning fasteners, inserted through the bone wall, with the apertures. One known technique is the use of a jig that is accurately retained in relationship to the nail by a portion extending into the bone through the opening made in the proximal end of the bone and which has an external portion that extends parallel the bone with alignment means for aligning fasteners with the apertures in the nail provided along the external portion. While such a technique is quite successful at accurately locating the proximal locking fastener(s), the rather long distance to the distal fasteners allows relative movement between the jig and the nail which distorts the alignment means. Accordingly, alignment with the distal aperture(s) is not assured and damage to the bone wall or to the nail aperture may result.

A more accurate technique for locating the distal apertures is an X-ray imaging technique that utilizes a target device. The target device is positioned at the approximate location of the distal nail aperture and iteratively repositioned until a perfect circular image of the nail aperture is produced. This occurs when the target device is located on the centerline of the aperture. Means are provided, relative to the target device, to then locate the insertion point for the fasteners. The problem with such a distal aperture location technique is the cumulative exposure of the patient and the operating team to X-ray radiation which can be excessive if the procedure to properly position the target device results in a large number of attempts. Also, if correct alignment is not obtained, damage to the bone or nail may jeopardize the fixation.

SUMMARY OF THE INVENTION

The present invention provides a method and apparatus for reducing a fracture in a long bone and for producing longitudinal tension between the segments of the bone including an improved technique for location of the distal nail apertures and alignment of the distal locking fasteners with the apertures.

An orthopedic nail according to the invention is dimensioned substantially to conform to the shape of the intramedullary canal of the bone to be fixed and has a first terminal end with edge means defining a mouth extending axially outwardly to the terminal end. The mouth has an inward bight portion and a pair of side edge portions that extend outwardly from the bight portion to the terminal end.

A method of fixation of a fracture according to the invention includes making an opening sufficiently large to pass the nail in one end portion of the bone, such as the proximal end, and inserting the nail, terminal end first, in the opening. The nail is axially extended through the medullary canal into the opposite, or distal, bone segment with the mouth bight portion oriented generally on a frontal plane. A fastener of diameter substantially smaller than the separation of the mouth side edge portions is inserted transversely through the bone on a medial frontal plane at an estimated location between the side edge portions within the nail mouth. The fastener should be received within the wide mouth of the nail and subsequently seated against the bight portion by the axial movement of the nail. After the seating of the distal fastener is verified, a proximal locking device is installed according to conventional techniques. If a second distal fastener is indicated, an alignment jig according to the invention is provided to accurately locate the position of a transverse distal aperture proximate the mouth and align the fastener with the aperture. In a preferred embodiment, a special insertion tool is provided to substantially close the mouth during movement through the medullary canal to reduce the snagging of vessels.

The invention is capable of significantly reducing the cumulative exposure to X-ray radiation and reducing the likelihood that damage to the bone or the nail may result in abandonment of the procedure or inadequate fixation. In addition, the present invention avoids the requirement for an incision at the fracture site and substantially reduces the severity of the incision required at the distal fastener site. In addition, the invention is efficient because it requires only one insertion tool and alignment jig set for a particular bone for the multiplicity of nail sizes required to fix fractures due to the variation in patient bone size.

These and other related objects, advantages and features of this invention will become apparent upon review of the following specification in conjunction with the drawings.

BRIEF DESCRIPTION OF THE DRAWINGS

FIG. 1 is a sagittal view of an orthopedic nail according to the invention;

FIG. 2 is the orthopedic nail in FIG. 1 rotated 90° about a longitudinal axis;

FIG. 3 is an enlarged sectional view of an orthopedic nail taken along the lines III—III in FIG. 1;

FIG. 4 is a front view of a bone having a compound fracture therein, illustrating a distal guide pin being driven into the bone according to the method of the invention;

DESCRIPTION OF THE PREFERRED EMBODIMENT

Figures 5, 6:
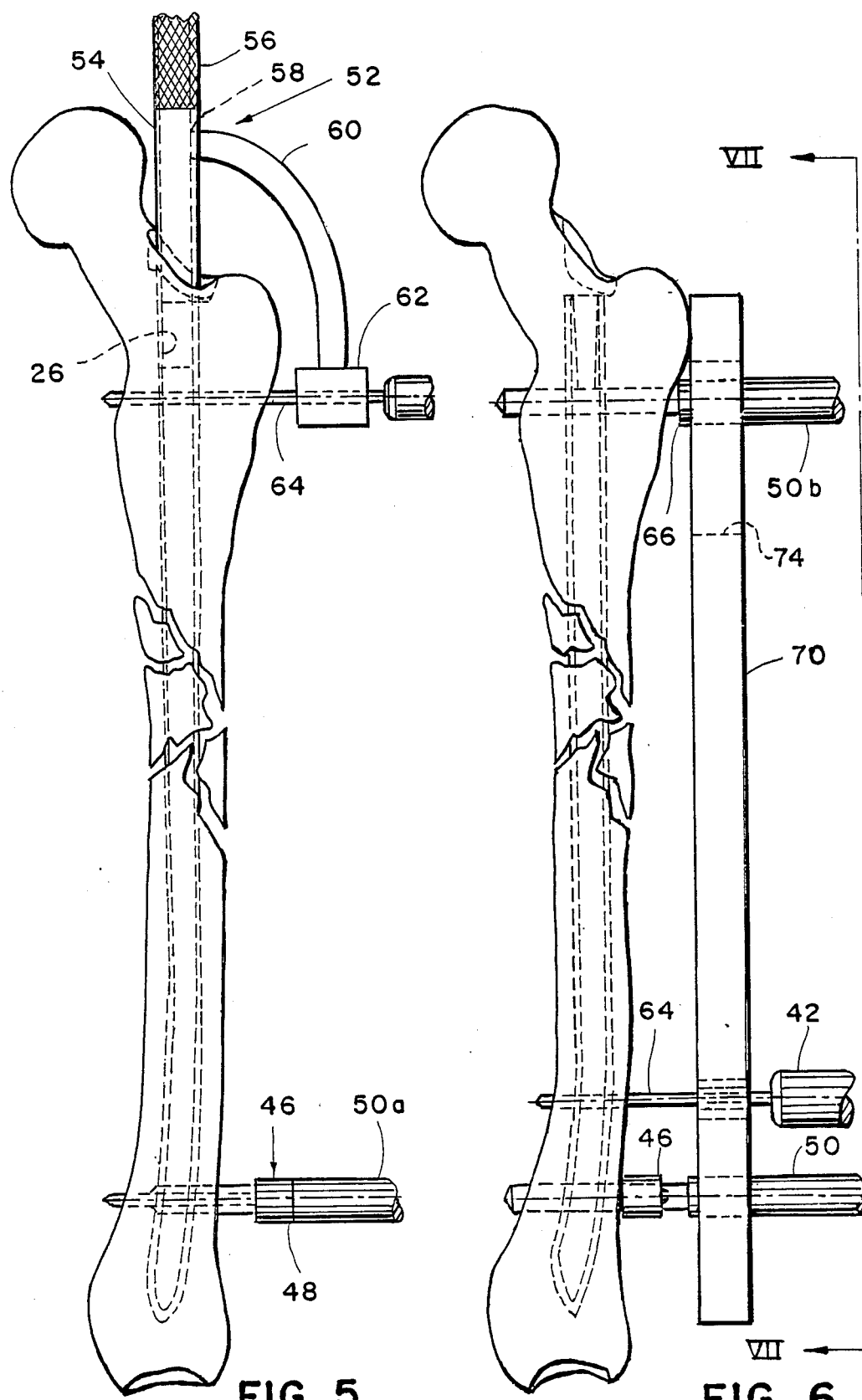
FIG. 5 is the same view as FIG. 4 illustrating attachment of a cannulated distal fastener and the use of a proximal alignment jig to attach the proximal locking fastener according to the method of the invention.
FIG. 6 is the same as FIGS. 4 and 5 showing the use of a second-distal-fastener alignment jig according to the invention to locate a second distal fastener.

Referring now specifically to the drawings, and the illustrated embodiments depicted therein, an elongated orthopedic nail 10 is dimensioned to substantially conform to the shape of the medullary canal of the bone to be fixed (FIG. 1). Nail 10 has a first, terminal end 12 and an edge means 14 defining a mouth 15 extending axially outwardly toward end 12. Edge means 14 includes an inward bight portion 16 and a pair of side edge portions 18a and 18b extending away from the bight portion 16. In one embodiment, side edge portions 18a, 18b diverge outwardly from the bight portion. A first transverse aperture 20 extends through opposing wall portions of nail 10 at a second, opposite end 13 thereof spaced a first predetermined longitudinal distance X from a second end 13 of the nail. An optional second transverse aperture 22 extends through opposing wall portions of nail 10 spaced a second predetermined longitudinal distance Y from bight portion 16.

Nail 10 is made from an alloy such as titanium alloy and is tubular, having a wall 25 defining an outer wall surface 24 and an inner wall surface 26 (FIG. 3). Inner wall surface 26 is threaded for the outermost several centimeters at second end 13. A pair of transverse slot portions 28a and 28b are formed in nail wall 25 at second end 13.

Referring to FIG. 4, a long bone, such as a femur, is shown at 30 severed into a first, proximal bone segment 34 and a second, distal bone segment 36 at fraction site 32. In order to reduce the fracture and provide longitudinal tension between the bone segments 34 and 36, an opening 38 is made, which in the illustrated embodiment, is in the proximal end 39 of bone 30, by conventional techniques. Opening 38 is illustratively located in the trochanteric fossa and is reamed to a diameter 1 or 2 millimeters greater than the diameter at the widest portion of nail 10. Bone segments 34 and 36 are reduced by manual manipulation and terminal end 12 of nail 10 is inserted through opening 38 into the medullary canal. With bight 16 oriented on a generally frontal plane, nail 10 is axially extended through the medullary canal until it is substantially enclosed within bone 30. Care must be taken to assure bight 16 is oriented on a generally frontal plane after insertion. Slot portions 28a, 28b, which are oriented on the same plane as bight portion 16 in the illustrated embodiment, may be used as indicating means for indicating the angular orientation of the nail.

A sagittal, cutaneous incision is made at the distal portion of the leg in the vicinity where mouth 15 is estimated to be located. In one embodiment, a guide pin 40 is percutaneously inserted transverse the bone on a medial frontal plane by the use of a drill 44. Pin 40 has a tip with cutting means thereon (not shown) to penetrate the bone and is rotatably held in the drill by a chuck 42. After guide pin 40 is inserted within the bone, the drill and chuck are detached therefrom and conventional imaging technique is used to determine the position of pin 40 with respect to mouth 15. If pin 40 is located between sidewall 18a and 18b it is thus within mouth 15. If it is determined that pin 40 has not been successfully located within mouth 15, then a second transverse guide pin is inserted percutaneously in the same fashion and imaging technique is utilized to determine that the second guide pin has been positioned within mouth 15. No special targeting device is needed in association with the disclosed imaging techniques and no more than two exposures should be required to position a guide pin within mouth 15.

With guide pin 40 positioned within mouth 15, a distal fastener 46 is inserted into the bone cannulated with guide pin 40 (FIG. 5). In a preferred embodiment, fastener 46 is a hollow, 6.5 mm, self-tapping screw made from a titanium alloy or the like and which has a head 48 with a hex or fluted socket that is selected to be compatible with the tip of a screwdriver shaft 50a. Such a fastener is manufactured by Orthomed Company. Because distal fastener 46 is hollow, it can be cannulated with guide pin 40 to assure successful insertion into bight portion 16 of mouth 15. With fastener 46 positioned within mouth 15, nail 10 is then further axially thrust to seat bight portion 16 against the distal fastener.

An alternative method for seating bight portion 16 against distal fastener 46 is to first drill a transverse distal opening on the medial-frontal plane of the bone and attach the distal fastener to the bone walls. A nail, in which the mouth side edge portions preferably diverge outwardly, is inserted through opening 38 into the medullary canal and axially extended through the canal. Bight portion 16 must be oriented on the same plane as the distal fastener, as mouth 15 approaches the distal fastener. With bight portion 16 and the distal fastener on the same plane, the diverging walls of the mouth will receive the fastener and seat the bight portion against it.

After the distal fastener is attached, a conventional technique may be used to lock proximal bone segment 34 to the nail. In the illustrated embodiment, a proximal fastener alignment jig 52 is attached to second end 13 of nail 10 by a threaded shaft 58 that extends through a hollow body 54 and threadably engages the threads on inner wall surface 26 (FIG. 5). A pair of ears (not shown) on body 54 may be provided to engage transverse slot portions 28a and 28b in order to angularly orient alignment jig 52 with the nail. A handle 56 extending from shaft 58 may be provided. A lateral arm 60 extends from body 54 and terminates in an apertured socket 62. The location of socket 62 and the axial aperture therein, are preselected to be in axial alignment with aperture 20 in the nail. A diameter-reducing sleeve (not shown) may be inserted into socket 62 and a drill bit 64 of a diameter to fit the sleeve is passed through the socket 62 and transversely through the bone using drill 44. The drill bit and sleeve are removed and a self-tapping proximal fastener 66 is engaged by the tip of a screwdriver blade 50b, inserted through socket 62 and threaded into the proximal opening formed by the drill in the bone. Because of the predetermined orientation of alignment jig 52 with nail 10, proximal fastener 66 will be aligned with aperture 20 and will pass therethrough.

Figure 7:
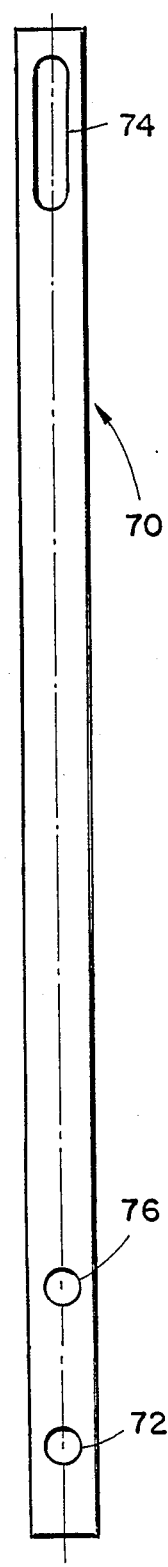
FIG. 7 is an enlarged sagittal view of the second-distal-fastener alignment jig taken along the lines VII—VII of FIG. 6.

The previously described procedure will, in many circumstances, be sufficient to retain bone segments 34 and 36 in tension and prevent longitudinal shrinkage of the bone length. If indicated, a second distal fastener may be inserted by the use of a distal fastener alignment jig 70 (FIGS. 6 and 7). Jig 70 is an elongated member having an edge means defining circular openings 72 and 76 at one end thereof and a slotted opening 74 at an opposite end thereof passing entirely through the jig. Openings 72 and 76 are spaced apart by the Y dimension and slotted opening 74 is spaced from opening 72 so as to include within its perimeter the proximal fastener.

In use, opening 72, which is slightly larger than screwdriver shaft 50a, is generally aligned with distal fastener 46 and screwdriver shaft 50a or the like passed through opening 72 and engaged with distal fastener 46 (FIG. 6). This provides means for longitudinally orienting the jig with the nail. The slotted opening 74 is aligned with proximal fastener 66 and a screwdriver shaft 50b, or the like, is passed through opening 74 and is engaged with fastener 66. This provides means for orienting alignment jig 70 on the same frontal plane as the nail.

With jig 70 properly positioned, opening 76 will be aligned with the centerline of aperture 22 and provide means for aligning the second distal fastener with aperture 22. A sleeve (not shown) is placed in opening 76 to reduce the diameter to the appropriate size and a drill bit 64, driven by a drill 44, is passed through the sleeve to make a transverse opening in the bone. The drill bit will pass through the aperture 22 in nail 10 as it drills through the bone. Drill bit 64 and the sleeve are withdrawn and a second distal fastener (not shown) is inserted through opening 76 in jig 70 and into the bone using a screwdriver shaft 50a.

The reason for slotting opening 74 is to accommodate the multiplicity of nail sizes that are required to provide fixation of a particular long bone on various patients. The distance between the distal fastener and the proximal fastener will vary depending on the length of the nail. However, the distance between the two distal fasteners Y may be, and preferably is, constant for all nail sizes for a particular bone. Thus, one jig 70 may be used to accurately position the second distal fastener for all such nail sizes.

Figure 8:
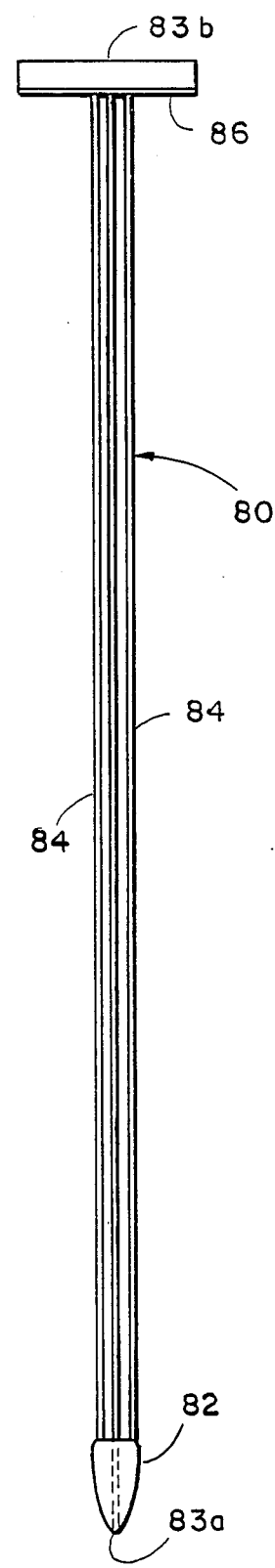
FIG. 8 is an enlarged anterior view of an orthopedic nail insertion device according to the invention.
Figure 9:
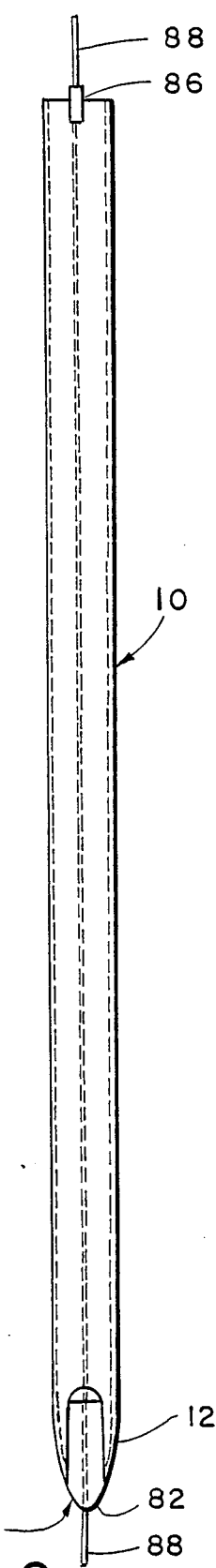
FIG. 9 is an enlarged sagittal view of a preferred embodiment of the apparatus prepared for axial insertion of the orthopedic nail in the medullary canal.

In a most preferred embodiment, the insertion of nail 10 into the medullary canal is preceded by the insertion of a guide wire 88 through opening 38 and into the medullary of the distal segment 36. Imaging is used to verify that guide wire 88 is properly positioned in the distal bone segment. With guide wire 88 in place, the nail 10 may be cannulated with the guide wire and inserted into the medullary canal. In order to reduce the likelihood that forwardly extending mouth 15 will snag vessels and the like as it is moved forwardly inside the medullary canal, a special insertion tool is provided. Insertion tool 80 has an elongated head 82 which is configured to the inside surface of terminal end 12 of the nail and which has a central axial shaft 83a defined therethrough (FIG. 8). Head 82 is connected to a T-handle 86 at an opposite end of the insertion tool by a multiplicity of elongated resilient members 84. A central axial shaft 83b is defined through T-handle 86 aligned with shaft 83a in the head. The purpose of resilient members 84 is to bias head 82 into engagement with the inside surface of terminal end 12 and to accommodate variation in spacing between the head and the T-handle so that one insertion tool may be used with various nail lengths. When head 82 is positioned inside nail 10 and forwardly within mouth 15 it substantially closes the mouth (FIG. 9). Accordingly, mouth 15 will be less likely to snag vessels during insertion.

In use, insertion tool 80 is inserted telescopingly within nail 10. The T-handle 86 is received within transverse slot portions 28 and head 82 is biased by members 84 fully forward inside the nail. With the insertion tool within the nail, the assembly is inserted into the medullary canal cannulated with guide wire 88, which is telescopingly received within shafts 83a and 83b. The T-handle may be used to provide forward thrust to the nail and to control the rotational alignment of the nail during insertion. Once the nail is substantially fully inserted within the medullary canal, a rearward pull on T-handle 86 will withdraw the insertion tool. The guide wire 88 is also then withdrawn.

With the nail properly inserted in the medullary canal, the insertion tool and guide wire withdrawn and the proximal and distal fasteners inserted, the incisions are closed in a conventional fashion.

Changes and modifications in the specifically described embodiments can be carried out without departing from the principles of the invention which is intended to be limited only by the scope of the appended claims.

The embodiments of the invention in which an exclusive property or privilege is claimed are defined as follows:

1. A method for intramedullary fixation of a fracture in a long bone by reduction of the fracture and longitudinal extension of the bone segments on the opposite sides of said fracture comprising the steps of:

selecting an elongated nail contoured to substantially conform to the shape of the medullary canal of the bone to be fixed, said nail having means defining a distal portion having a terminal end thereof and edge means defining a mouth in said distal portion, said mouth having an inward bight portion and a pair of side edge portions extending outwardly from said bight portion to said terminal end, said distal portion adapted to envelop and nest a first fastener in said mouth at said bight portion upon convergence with said first fastener when said first fastener is extending transverse to the direction of elongation of said nail between opposite wall portions of the bone, said nail further having a proximal end opposite said terminal end and means defining a first transverse aperture a first predetermined distance from said proximal end;

making an opening in the proximal end of said bone sufficiently large to pass said nail;

inserting said terminal end of said nail into said medullary canal through said opening and substantially through said medullary canal in a manner that said terminal end is positioned in a distal portion of said medullary canal with said bight portion oriented generally on a predetermined plane;

attaching a first fastener at said distal end portion of said bone transversely through the medullary canal thereof and oriented generally on said predetermined plane; whereby said fastener will be received by said mouth; and attaching a second fastener transverse said bone in said medullary canal spaced from said nail proximal end by said predetermined distance, whereby said second fastener will extend through said aperture in said nail.

2. The method in claim 1 wherein said step of inserting is performed before said step of attaching.

3. The method in claim 2 wherein said step of attaching includes driving a first guide pin into said bone and determining whether said pin is in said mouth.

4. The method in claim 3 further including driving a second guide pin into said bone if said first guide pin is not in said mouth and determining whether said second guide pin is in said mouth.

5. The method in claim 3 wherein said first fastener has means defining a longitudinal passage therethrough and said step of attaching further includes screwing said first fastener into said bone if said pin is in said mouth, said passage surrounding said pin.

6. The method in claim 4 wherein said first fastener has means defining a longitudinal passage therethrough and said step of attaching further includes screwing said first fastener into said bone if said second guide pin is in said mouth, said passage surrounding said second guide pin.

7. The method in claim 1 wherein said first nail further has means defining a second transverse aperture spaced a second predetermined distance from said bight and further including the step of attaching a third fastener transverse said bone in said medullary canal spaced from said first fastener by said second predetermined distance, whereby said third fastener will extend through said second transverse aperture.

8. The method in claim 7 wherein said step of attaching said third fastener further includes juxtaposing a jig adjacent said bone, said jig having longitudinal alignment means for longitudinally orienting said jig with said nail, plane alignment means for orienting the jig on the same frontal plane as said nail and means for aligning said third fastener with said second aperture.

9. The method in claim 8 wherein said plane alignment means comprises a longitudinally elongated slot on said jig and a shaft extending from said second fastener in said slot.

10. The method in claim 8 wherein means for aligning said third fastener includes an opening through said jig and wherein said step of attaching said third fastener further includes extending a drill bit through said jig opening, drilling a hole through the bone, withdrawing the drill and inserting said third fastener through said jig opening.

11. A method for intramedullary fixation of a fracture in a long one by reduction of the fracture and longitudinal extension of the bone segments on opposite sides of said fracture comprising the steps of:
selecting an elongated nail contoured to substantially conform to the shape of the medullary canal of the bone to be fixed, said nail having means defining a distal portion having a terminal end thereof and edge means defining a mouth in said distal portion, said mouth having an inward bight portion and a pair of side edge portions extending outwardly from said bight portion to said terminal end, said nail further having a proximal end opposite said terminal end and means defining a first transverse aperture a first predetermined distance from said proximal end;
making an opening in the proximal end of said bone sufficiently large to pass said nail;
inserting said terminal end of said nail into said medullary canal through said opening with said bight portion oriented generally on a frontal plane;
attaching a first fastener at the distal portion of said bone transversely through the medullary canal thereof and oriented on said frontal plane; whereby said fastener will be received by said mouth; and
attaching a second fastener transverse said bone in said medullary canal spaced from said nail proximal end by said predetermined distance, whereby said second fastener will extend through said aperture in said nail;
wherein said nail has means defining an internal axial cavity therethrough and wherein said step of inserting further includes extending an elongated guide wire to said bone distal portion medullary canal through said opening, telescoping an insertion device into said cavity, said insertion device having a head dimensioned to substantially close said mouth and means defining a bore therethrough, and cannulating said insertion means bore with said guide wire.

12. The method in claim 11 further including removing said insertion device and said guide wire after said step of axially thrusting said nail.

13. A method for intramedullary fixation of a fracture in a long bone by reduction of the fracture and longitudinal extension of the bone segments on opposite sides of said fracture comprising the steps of:
selecting an elongated nail contoured to substantially conform to the shape of the medullary canal of the bone to be fixed, said nail having means defining a distal portion having a terminal end thereof and edge means defining a mouth in said distal portion, said mouth having an inward bight portion and a pair of side edge portions extending outwardly from said bight portion to said terminal end said distal portion adapted to envelop and nest a first fastener in said mouth at said bight portion upon convergence with said first fastener when said first fastener is extending transverse to the direction of elongation of said nail between opposite wall portions of the bone;
making an opening in the proximal end portion of said bone sufficiently large to pass said nail;
inserting said nail through said opening into said medullary canal with said terminal end leading;
attaching a first fastener transverse the distal bone segment, said bight and said fastener being on substantially the same plane causing said fastener to rest within said bight when a proximal portion of said nail opposite said terminal end is locked to the proximal bone segment, whereby compression of the fracture will be prevented.

14. The method in claim 13 in which said side edge portions diverge outwardly and in which said step of attaching precedes said step of inserting.

15. The method in claim 13 wherein said step of attaching a first fastener follows said step of inserting said nail and comprises driving a guide pin into said bone, determining whether said guide pin is in said mouth and attaching said first fastener transverse said bone in relationship to said guide pin.

16. The method in claim 15 wherein said first fastener is hollow and cannulated with said guide pin.

17. The method in claim 13 wherein said nail further has a proximal end opposite said terminal end and means defining an aperture spaced a predetermined distance from said proximal end and further including the step of attaching a second fastener transverse said bone in said medullary canal spaced from said proximal end by said predetermined distance, whereby said second fastener will extend through said aperture.

18. A method for intramedullary fixation of a fracture in a long bone by reduction of the fracture and longitudinal extension of the bone segments on opposite sides of said fracture comprising the steps of:

selecting an elongated nail contoured to substantially conform to the shape of the medullary canal of the bone to be fixed, said nail having means defining a distal portion having a terminal end thereof and edge means defining a mouth in said distal portion, said mouth having an inward bight portion and a pair of side edge portions extending outwardly from said bight portion to said terminal and;

making an opening in the proximal end portion of said bone sufficiently large to pass said nail;

inserting said nail through said opening into said medullary canal with said terminal end leading;

attaching a first fastener transverse the distal bone segment, said bight and said fastener being on substantially the same plane causing said fastener to rest within said bight when the proximal portion of said nail opposite said terminal end is locked to the proximal bone segment, whereby compression of the fracture will be prevented;

wherein said step of inserting said nail further includes providing insertion means for closing said mouth and removing said insertion means after said nail is substantially inserted.

19. The method in claim 18 wherein said step of inserting said nail further includes inserting a guide wire through said opening into said one bone segment and inserting said nail with said insertion means cannulated said guide wire.

20. An orthopedic nail for intramedullary fixation of a fracture in a long bone by reduction of the fracture and longitudinal extension of the bone segments, said nail comprising an elongated body configured to substantially conform to the shape of the medullary canal of a bone to be fixed; means defining a first portion having a terminal end thereof; and edge means defining a mouth in said first portion, said mouth having an inward bight portion and a pair of side edge portions extending outwardly from said bight portion to said terminal end, and said first portion adapted to envelop and nest a first fastener in said mouth at said bight portion upon convergence with said first fastener when said first fastener is extending transverse to the direction of elongation of said nail between opposite wall portions of the bone.

21. The orthopedic nail in claim 20 further including a second end opposite said terminal end and means defining a first transverse aperture spaced a first predetermined distance from said second end.

22. The orthopedic nail in claim 21 further including means defining a second transverse aperture therein spaced a second predetermined distance from said bight opposite said first end.

23. The orthopedic nail in claim 20 in which said side edge portions diverge away from said bight portion.

24. The orthopedic nail in claim 20 wherein said nail is tubular in shape defining an internal axial cavity therethrough extending to said mouth from a second end opposite said terminal end and wherein said nail further includes an elongated removable insertion means for closing said mouth said insertion means extending to said mouth in said cavity and removable from said second end.

25. The orthopedic nail in claim 24 in which said insertion means comprises a head configured to the inside contour of said first end portion retraction means for retracting said heat from said inside said nail.

26. An orthopedic nail for intramedullary fixation of a fracture in a long bone by reduction of the fracture and longitudinal extension of the bone segments, said nail comprising a body configured to substantially conform to the shape of the medullary canal of a bone to be fixed; means defining a first portion having a terminal end thereof; and edge means defining a mouth in said first portion, said mouth having an inward bight portion and a pair of side edge portions extending outwardly from said bight portion to said terminal end; and removable insertion means for closing said mouth, said insertion means comprises a head configured to the inside contour of said first portion and retraction means for retracting said head from inside said nail, wherein said retraction means comprises a handle and means comprising elongated resilient members connecting said handle to said head.

27. The orthopedic nail in claim 26 in which said insertion means has means defining aligned axial bores in said head and said handle.

28. In a nail particularly adapted for intramedullary fixation of a fracture in a long bone such that adjacent bone segments at the fracture site are restrained from compression one against the other, and wherein said nail is longitudinally locked to the bone on both sides of said bone, the improvement comprising edge means defining a mouth nested on one said fastener, said mouth having an inward bight portion and a pair of side edge portions extending axially outwardly from said bight through the end of the nail whereby said mouth will envelop one said fastener extending between opposite wall portions of the bone at said bight.

29. The nail in claim 28 in which said side edge portions diverge away from said bight portion.

* * * * *

UNITED STATES PATENT AND TRADEMARK OFFICE
CERTIFICATE OF CORRECTION

PATENT NO. : 4,846,162

DATED : July 11, 1989

INVENTOR(S) : H. David Moehring

It is certified that error appears in the above-identified patent and that said Letters Patent is hereby corrected as shown below:

Column 1, line 20:

"looked" should be --locked--.

Column 7, line 19:

After "said" delete "first".

Column 8, line 1:

After "oriented" insert --generally--.

Column 9, line 13:

"and" should be --end--.

Column 10, line 18:

"heat" should be --head--.

Column 10, line 44:

After "said" insert --fracture by a fastener passing transversely through said--.

UNITED STATES PATENT AND TRADEMARK OFFICE
CERTIFICATE OF CORRECTION

PATENT NO. : 4,846,162

DATED : July 11, 1989

INVENTOR(S) : H. David Moehring

It is certified that error appears in the above-identified patent and that said Letters Patent is hereby corrected as shown below:

Column 10, line 50:
    After "bone" insert --and upon convergence therewith nest said fastener--.

Signed and Sealed this

Twenty-eighth Day of May, 1991

*Attest:*

HARRY F. MANBECK, JR.

*Attesting Officer*      *Commissioner of Patents and Trademarks*